(12) United States Patent
Echner et al.

(10) Patent No.: US 9,031,204 B2
(45) Date of Patent: May 12, 2015

(54) LEAF MODULE FOR A MULTI-LEAF COLLIMATOR AND MULTI-LEAF COLLIMATOR

(75) Inventors: Gernot Echner, Wiesenbach (DE); Steffen Seeber, Heidelberg (DE); Klaus Schewiola, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 40 days.

(21) Appl. No.: 14/117,693

(22) PCT Filed: May 15, 2012

(86) PCT No.: PCT/EP2012/058980
§ 371 (c)(1),
(2), (4) Date: Dec. 12, 2013

(87) PCT Pub. No.: WO2012/156389
PCT Pub. Date: Nov. 22, 2012

(65) Prior Publication Data
US 2014/0217312 A1 Aug. 7, 2014

(30) Foreign Application Priority Data

May 17, 2011 (EP) .................................... 11166333

(51) Int. Cl.
*G21K 1/04* (2006.01)
*A61N 5/10* (2006.01)

(52) U.S. Cl.
CPC .............. *G21K 1/046* (2013.01); *A61N 5/1045* (2013.01)

(58) Field of Classification Search
USPC .......... 250/359.1, 361 R, 362, 363.01, 363.1, 250/370.08, 370.09, 505; 378/63–65, 378/145–147, 150–152
See application file for complete search history.

(56) References Cited

U.S. PATENT DOCUMENTS

| 4,794,628 | A | * | 12/1988 | Sakamoto et al. | .............. 377/28 |
| 4,794,629 | A | | 12/1988 | Pastyr et al. | |
| 5,557,107 | A | * | 9/1996 | Carcreff et al. | ........... 250/361 R |
| 7,242,750 | B2 | | 7/2007 | Tsujita | |

(Continued)

FOREIGN PATENT DOCUMENTS

WO WO 2009/036813 A1 3/2009

OTHER PUBLICATIONS

International Application PCT/EP2012/058980 filed May 15, 2013, International Search Report mailed Aug. 6, 2012.

(Continued)

*Primary Examiner* — Bernard E Souw
(74) *Attorney, Agent, or Firm* — Woodard, Emhardt, Moriarty, McNett & Henry LLP

(57) ABSTRACT

A leaf module for a multi-leaf collimator comprises a leaf unit and a leaf drive unit. The leaf unit comprises a leaf for shielding beams from a selected area. The leaf unit is mounted displaceably in an adjusting direction with relation to the leaf drive unit. The leaf drive unit is designed to displace the leaf unit linearly in the adjusting direction. The leaf drive unit comprises at least one drive mechanism which operates based on piezoelectric actuation, being designed such that the leaf drive unit thoroughly encloses the leaf unit within a plane being oriented substantially perpendicularly related to the adjusting direction. The multi-leaf collimator can comprise a plurality of leaf modules while being shaped as compact as possible. Both precise and stable adjustability of the leaf unit is achieved with the leaf module.

18 Claims, 9 Drawing Sheets

(56) References Cited

U.S. PATENT DOCUMENTS

Figure 1:
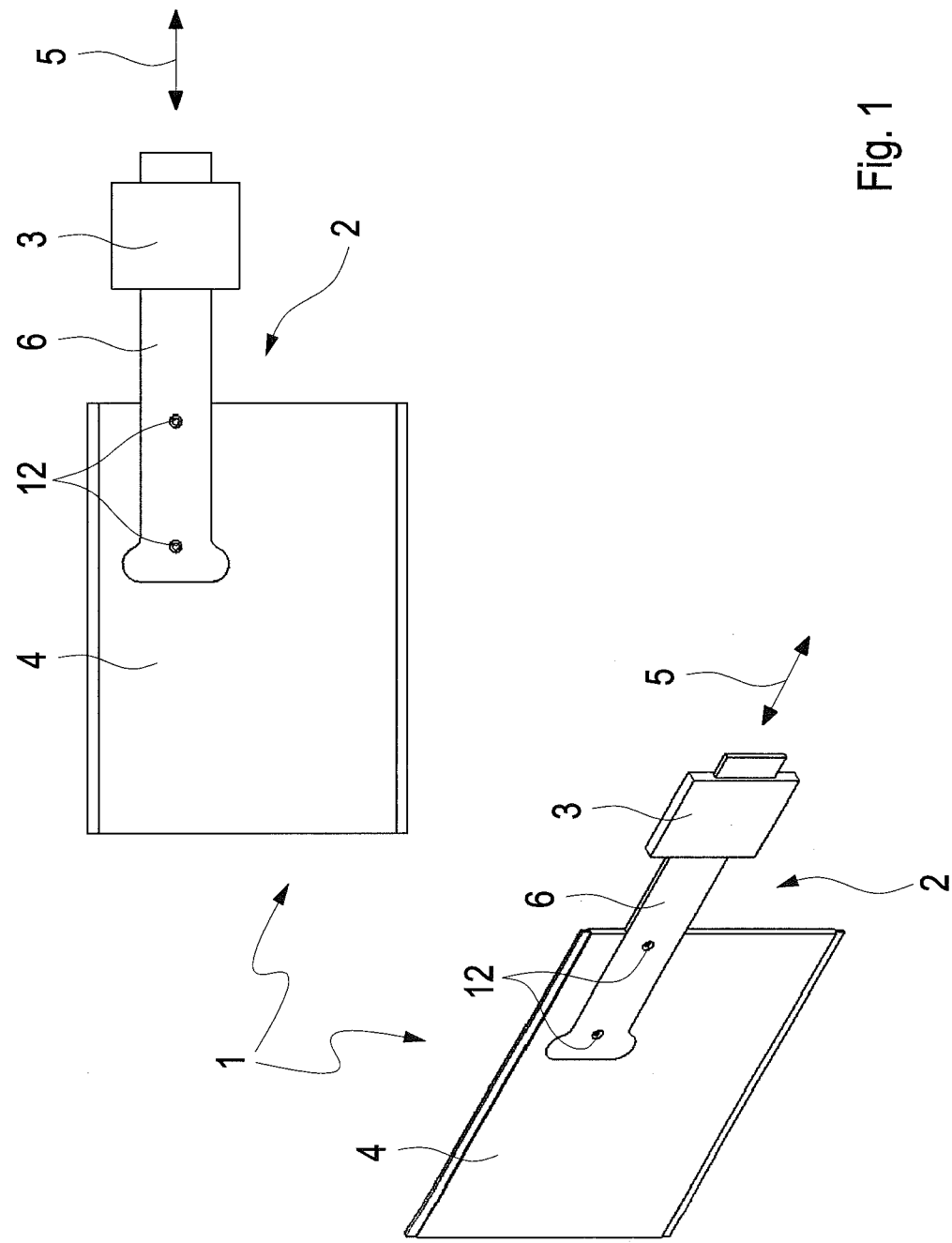

| | | | |
|---|---|---|---|
| 8,384,049 B1* | 2/2013 | Broad | 250/492.1 |
| 2003/0063266 A1* | 4/2003 | Leenders et al. | 355/53 |
| 2006/0067480 A1* | 3/2006 | Juschka et al. | 378/150 |
| 2008/0191583 A1* | 8/2008 | Bohn | 310/329 |
| 2009/0041199 A1* | 2/2009 | Bohn | 378/152 |
| 2010/0278310 A1* | 11/2010 | Dehler et al. | 378/150 |
| 2014/0288349 A1* | 9/2014 | Seeber et al. | 600/1 |

OTHER PUBLICATIONS

International Application PCT/EP2012/058980 filed May 15, 2013, International Preliminary Report on Patentability mailed Nov. 28, 2013.

* cited by examiner

LEAF MODULE FOR A MULTI-LEAF COLLIMATOR AND MULTI-LEAF COLLIMATOR

The invention relates to a leaf module for a multi-leaf collimator, comprising a leaf unit and a leaf drive unit, wherein the leaf unit comprises a leaf for shielding beams from a selected area, the leaf unit is mounted displaceably in an adjusting direction with relation to the leaf drive unit, wherein the leaf drive unit is designed to displace the leaf unit linearly in the adjusting direction, and the leaf drive unit comprises at least one drive mechanism which operates based on piezoelectric actuation. Additionally, the invention relates to a multi-leaf collimator.

Various embodiments of multi-leaf collimators comprising leaf modules each featuring a leaf unit and a leaf drive unit are known in the art. Multi-leaf collimators of such kind are preferably employed for controlling a shape of a high-energy radiation beam emanating from a radiation source and propagating in a direction of propagation.

Multi-leaf collimators are commonly used in treatment devices for oncological radiation therapy. Said collimators delimit high-energy beams, in most cases high energy radiation of a linear accelerator, in such a way that the beams have exactly the same shape as the treatment object. Since such irradiation, e.g. of a tumor, occurs from various directions, it is possible to achieve a great irradiation intensity of the tumor and, at the same time, to stress the surrounding tissue only to a limited extent.

The leaves of the multi-leaf collimator may also be called "shutter blades" or "lamellae". The multi-leaf collimators may also be called contour collimators since due to the positioning of the leaves, contours of treatment objects, for example tumors, can be recreated for each beam application, each of which occurs from a certain solid angle. This is important in order to protect the adjacent healthy tissue to the greatest extent possible. In the case of organs at risk, such as spine or nerves, this is particularly necessary in order to preserve their functional capability.

A general example of a multi-leaf collimator comprising leaf modules, with a leaf unit and a leaf drive unit is obtainable from U.S. Pat. No. 4,794,629. In such multi-leaf collimators, each leaf unit must be moved into a certain position. Thus, in most cases, a leaf drive unit must be assigned to each leaf unit. According to the aforementioned publication, no separate motor is assigned to each leaf unit, which is why the leaf units are arranged in series by means of drive couplings and locking devices. However, it has also been known to assign an electric motor to each leaf unit that positions the leaf unit via a pinion and a gear rod-like drive engagement.

However, the more precisely the shape of the treatment object, e.g. of a tumor, is to be recreated, the more and thinner leaves within the leaf units will be required. This means that a large number of electric motors and drive transmissions within the leaf drive units being connected to the leaf units must be housed in an extremely small space. Also, the leaf modules are arranged in such manner that they will be located within one irradiation head containing the radiation source and the collimator.

During an irradiation treatment, the irradiation head usually has to be moved into various but defined angles with respect to the target volume, e.g. the tumor. Thus, it is desirable to design such a collimator as compact and lightweight as possible.

Further, when designing leaf modules for a multi-leaf collimator, the accuracy of the adjusting, i.e. the displacement of the leaf units in the adjusting direction with relation to the leaf drive unit, is a decisive factor both for therapeutic success of the irradiation treatment and for possible adverse effects due to misguided irradiation.

Several proposals have been made to employ drive mechanisms operating based on piezoelectric actuation within leaf drive units of leaf modules. General advantages of piezoelectric actuation, in particular by piezoelectric motors, may be identified as the high dynamics, the high positioning accuracy and the low impact of noise within the human acoustic range. Furthermore, piezoelectric motors may exert a clamping force on adjacent parts even when not being in operation. Also, piezoelectric motors do not emit a disruptive magnetic field as conventional electric motors do. This advantage particularly applies to the novel technique of combining imaging by magnetic resonance and radiation therapy with linear acceleration (MR-Linac). In this regard, the strong magnetic field established by the MRT will not disrupt conventional electric motors, as these are replaced by piezoelectric actuation. On the other hand, piezoelectric motors will not build a magnetic field disrupting the MR-imaging and/or the linear acceleration.

US 2010/0278310 A1 discloses a multi-leaf collimator with rotatory electromechanical motor and operating method. The electromechanical motor may be a piezo motor. The piezo motor engages leaf units by means of a toothing in order to displace the leaf units. However, indirect transmission of the piezo motor actuation via the proposed toothing involves a backlash concerning the accuracy of displacement of the leaf unit. Furthermore, inevitable slackness within the toothed transmission represents a further major backlash. When the irradiation head is moved in the manner described above, variations in the position of the irradiation head result in changes to the adjusting position of the leaf units, because the weight of the leaf units interacting with the slackness in the toothing within the transmission and/or within the guidance of the leaf unit displacement will result in unwanted deviation of leaf unit adjustment.

U.S. Pat. No. 7,242,750 B2 discloses a radiotherapy apparatus comprising a radiation source configured to radiate a radiation ray, a multi-leaf collimator, including a plurality of leaves, configured to limit a radiation range of the radiation ray and a drive unit configured to move at least one of the leaves with an ultrasonic wave. However, this publication does not explicitly address the disadvantageous effects of slackness within the transmission and/or guiding between leaf drive unit and leaf unit as observed in the course of the present invention and as described above.

A linear drive and a method for displacing an object by a linear drive, wherein the linear drive comprises at least one piezoelectric actuator, has been proposed by US 2008/0191583 A1.

Referring publication US 2009/0041199 A1 discloses a multi-leaf collimator and radiation therapy device basically employing aforesaid linear drive and method. This printed publication discloses a leaf module for a multi-leaf collimator and a multi-leaf collimator of the kind mentioned at the beginning of this specification.

The leaf module according to US 2009/0041199 A1 employs a drive mechanism comprising a piezoelectric actuator. The piezoelectric actuator comprises a piezoelectric element and a transducer coupled thereto, wherein a frictional force is transmitted between the transducer and the leaf unit as a driving force.

However, the frictional force sectionally applied by the transducer to the leaf unit may result in lateral displacement of the leaf unit in a direction being oriented perpendicularly related to the adjusting direction. Further linear guiding of the leaf unit has to be provided, resulting in further frictional force and thus in inaccuracy of adjustment.

When the transducer travels backwards with relation to the leaf unit and the direction of displacement, further unwanted deviation of the leaf unit may occur. When applying a plurality of piezoelectric actuators, however, the leaf module will no longer exhibit compact proportions.

The invention is therefore based on the objective of designing a leaf module for a multi-leaf collimator and a multi-leaf collimator of the kind mentioned at the beginning, respectively, in such a way that with a design of the leaf module being as compact as possible, both precise and stable adjustability of the leaf unit is achieved.

This objective is attained in accordance with the invention by the subject-matter disclosed in the independent claims. Preferred embodiments which may be realized in an isolated way or in combination with other preferred embodiments are disclosed subsequently and in the dependent claims.

Thus, in a first major aspect of the present invention, a leaf module for a multi-leaf collimator of the kind mentioned at the beginning is designed in such a way that the leaf drive unit thoroughly encloses the leaf unit within a plane being oriented substantially perpendicularly related to the adjusting direction.

The term "substantially perpendicular" as used herein refers to an orientation which the skilled person would still consider as being a perpendicular orientation, i.e. an orientation with a deviation up to an amount of ca. ±10° compared to a strictly perpendicular orientation.

The leaf module according to the invention is—with other words—designed in such a manner that the leaf drive unit clasps, embraces or encompasses the leaf unit within a plane being oriented in the way described above.

The portion of the leaf drive unit which encloses the leaf unit in the manner described needs, however, not necessarily exhibit a ring- or flange-like shape, even though such shaping will not depart from the character of the invention. It is rather essential that the leaf drive unit exhibits whatever shape necessary to enclose the leaf unit within a plane being oriented in the way described above.

With the leaf module according to the invention, any force being applied to the leaf unit and being oriented substantially perpendicularly to the adjusting direction, will be absorbed by the leaf drive unit itself, holding the leaf unit on the opposite side of the position where the force is being transmitted to the leaf unit. Thus, the transmission of such forces, in particular clamping, grasping and/or friction forces, no longer results in unwanted deflection of the adjustment of the leaf unit.

Owing to the aforementioned enclosing of the leaf unit, any movement of an irradiation head comprising the leaf module according to the invention will therefore not result in any deflection of the leaf unit either. Within the leaf module according to the invention, any slackness or play between the leaf unit and the leaf drive unit may be avoided. The leaf module according to the invention may be constructed in an extremely compact way and still allow highly precise adjustability of the leaf unit due to the enclosing of the leaf unit as described above. When being assembled or reassembled, no fine adjustment of the position of the leaf unit with relation to the leaf drive unit has to take place, as the interaction of these parts is preset by the enclosing of the leaf unit by the leaf drive unit. Due to a reduced number of parts, the possible compact shaping of the leaf module and less demand to (fine) adjusting tasks, the leaf module according to the invention may be produced with less effort and lower costs. Summarizing, while being shaped as compact as possible, both precise and stable adjustability of the leaf unit is achieved with the leaf module according to the invention.

The term "leaf unit" as used herein generally relates to a unit comprising a leaf. Therefore, in general, it is not necessarily required that the leaf unit comprises any other component apart from the leaf. However, without departing from the inventive idea, a leaf unit according to the term used herein may just as well comprise other parts aside from the leaf, as will be described below in detail.

The term "leaf drive unit" as used herein generally relates to a unit comprising at least one drive mechanism which works based on piezoelectric actuation, in particular a piezoelectric motor. However, a leaf drive unit according to the term as used herein may also comprise further components aside from a drive mechanism, in particular members for holding and/or housing a drive mechanism. With other words, a leaf drive unit according to the term as used herein may be provided by any construction which the skilled person would consider as being adapted to comprise at least one drive mechanism.

In a first optional and preferred embodiment of the leaf module according to the invention, the leaf drive unit is designed to displace the leaf unit in the adjusting direction and additionally provide guidance to the leaf unit with respect to any direction being oriented perpendicularly related to the adjusting direction. By combining the tasks to displace the leaf unit in the adjusting direction and additionally provide aforesaid guidance to the leaf within the leaf drive unit, a leaf module with compact design providing very precise and stable adjustability of the leaf unit may be obtained.

The term "guidance" as used herein refers to a technical effect achieved by appropriate means which properly impedes the leaf unit from deviating from the axis represented by the adjusting direction by a non-tolerable value.

In this optional embodiment, further guiding or guide elements assigned to the leaf unit and not comprised by the leaf drive unit may be constructed less complex compared to the known art or may even become unnecessary.

Preferably, the guidance of the leaf unit provided by the leaf drive unit is substantially free of slackness. According to this preferred embodiment, the tolerance for deviations of the leaf unit as explained above may be set as low that practically no noticeable slackness of the leaf unit with relation to the leaf drive unit will remain.

The term "substantially free of slackness" as used herein refers to a construction in which the skilled person will not notice any visible or tangible slackness, although some slackness in the microscopic range may be present, preferably a slackness of less than 0.1 mm, more preferably a slackness of less than 0.05 mm.

Any guidance provided by the leaf drive unit to the leaf unit, featuring some slackness or being substantially free of slackness, may preferably be obtained by any clamping, grasping, holding or friction force, or mixtures thereof, being exerted by the leaf drive unit on the leaf unit.

In particular, according to another optional embodiment, the leaf drive unit exerts a friction force and/or a clamping force on the leaf unit when no displacement of the leaf unit takes place. In most cases, but not mandatorily, a friction force and/or a clamping force will be exerted by the leaf drive unit when a displacement of the leaf unit takes place.

In an optional further embodiment of the leaf module according to the invention, one drive mechanism within the leaf drive unit encloses the leaf unit, or a plurality of separate drive mechanisms are arranged within the leaf drive unit in such manner that an enclosure of the leaf unit by the drive mechanisms is provided. With other words, according to this embodiment, one single drive mechanism, in particular a piezoelectric motor, may be provided enclosing the leaf unit. Alternatively, a plurality of separate drive mechanisms, in particular one drive mechanism on each side of the leaf unit, in particular wherein the drive mechanisms each comprise a piezoelectric motor, may be arranged within the leaf drive unit in such a way that said mechanisms form a thorough enclosure of the leaf unit within a plane being oriented substantially perpendicularly related to the adjusting direction.

Optionally, at least one drive mechanism comprised by the leaf drive unit may comprise a non-resonant piezoelectric motor. Non-resonant piezoelectric motors have been found to be able to offer much higher resolutions and higher forces than ultrasonic piezo motors can.

A non-resonant piezoelectric motor may comprise several individual piezo actuators.

Accordingly, in a further optional and preferred embodiment of the leaf module, at least one drive mechanism comprises a piezoelectric motor generating motion of the leaf unit through succession of coordinated clamping/unclamping and expanding/contracting cycles. Within the motion, each extension cycle may provide only a few microns of movement, but running at hundreds to thousands of Hertz, and achieving continuous motion with a range of up to several mm per second. Such piezoelectric motors are commercially available for instance from the Physik Instrumente (PI) GmbH & Co. KG company, Karlsruhe, Germany, inter alia under trademarks PiezoWalk®, NEXLINE® and NEXACT®.

In addition or alternatively, at least one drive mechanism within the leaf drive unit may comprise a piezoelectric motor featuring a piezoelectric element and a transducer coupled thereto. In function, a frictional force may be transmitted between the transducer and the leaf unit, wherein the piezoelectric actuator may move the leaf unit by the transducer in the direction of displacement. Opposite to the direction of displacement, the transducer may slide across the leaf unit in order to enable repeated movement of the leaf unit in the direction of displacement. Such drive mechanisms have been described in detail in aforementioned publications US 2008/0191583 A1 and US 2009/0041199 A1.

According to a further preferred optional embodiment of the leaf module, which may be combined with embodiments disclosed above or which may be realized independently, the leaf unit further comprises a guiding rod, wherein the guiding rod is a separate part being attached to the leaf, or wherein the guiding rod is an integral part of the leaf. In particular, the guiding rod according to this proposal may serve for intaking adjusting and/or guiding forces exerted by the leaf drive unit and transmitting such forces to the leaf. The guiding rod may extend substantially, i.e. with a deviation amounting up to ca. ±10°, in the adjusting direction of the leaf unit, i.e. the longitudinal axis of the guiding rod may substantially comply with the adjusting direction. Employing a guiding rod as proposed here yields several benefits. First of all, the leaf which normally comprises heavy and expensive material may be of smaller length, as the guiding rod will provide sufficient range for the displacement of the leaf unit. Consequently, the entire leaf module may be constructed lighter and more compact. Additionally, for the displacing and adjusting of the leaf unit, a defined interaction of the leaf drive unit with the guiding rod instead of the much larger leaf may be envisaged, yielding a substantial advantage with regards to the precision of adjustment.

Optionally, in a further embodiment, the guiding rod provides the portion of the leaf unit which is enclosed by the leaf drive unit. In such manner, the leaf drive unit enclosing the leaf unit may be constructed much smaller and with less weight. As a consequence, more leaves with smaller thickness may be provided within one irradiation head because adjacent leaf drive units, owing to their smaller shape will have less disposition to interfere with each other. Also, due to gained compactness of the coupling between smaller leaf drive units and the proposed guiding rods, much higher precision when adjusting the leaf units and less slackness concerning the guidance of the leaf units may be attained.

As a further option when employing a guiding rod, the guiding rod may comprise ceramic material and/or the guiding rod may be coated with ceramic material. Said ceramic material has been found to exhibit an advantageous interaction with drive mechanisms operating based on piezoelectric actuation, wherein beneficial clamping and/or friction forces may be transmitted to parts comprising or being covered with such ceramic material.

In particular relating to embodiments wherein a guiding rod is formed as an integral part of the leaf, at least one outer surface of the guiding rod may comprise a rail of ceramic material being attached to the guiding rod in an appropriate way. Such separate ceramic rails may for example be fixed to a guiding rod by a toothing connection and/or gluing and/or clamping.

Further optionally, related to embodiments comprising a guiding rod, the guiding rod may be attached to the leaf by form-fitting and/or force-locking, in particular wherein the guiding rod may be inserted into a channel located on the surface of the leaf, wherein the channel represents a negative pattern of the shape of the guiding rod. According to this embodiment, the guiding rod is safely and easily attachable to the leaf, nevertheless without enlarging the thickness of the leaf unit and thus retaining the compactness of the leaf unit and the entire leaf module. Hence, it will be preferred that the outer surface of the guiding rod and the surrounding surface of the leaf are arranged in one single joint plane.

In a further embodiment of the leaf module which is not restricted to the use of a guiding rod, the leaf material comprises a high density material, preferably tungsten. Tungsten has been found to have the capacity to very effectively shield beams from selected areas. A preferred embodiment of the leaf material comprises sintered material comprising approximately 95% tungsten and further components, in particular iron and/or nickel and/or copper. Alternatively, leaf materials with higher or lower fractions of tungsten compared to a preferred percentage of approximately 95% may be employed. Also, alternatively, a non-sintered material or even pure tungsten may be used as leaf material. Generally, any material, in particular high density material, which has the capacity to shield beams, may be employed as leaf material in order to implement the invention.

In a second major aspect of the invention, a multi-leaf collimator is disclosed, wherein the multi-leaf collimator comprises a plurality of leaf modules according to the invention. Relating to the essence and features of the multi-leaf collimator according to the invention, reference is at first made to all previous paragraphs of this specification. In other words, the essence and benefits of the multi-leaf collimator according to the invention will already become manifest from the previous paragraphs describing aspects of the leaf module. Also, it is obvious that within the multi-leaf collimator according to the invention, any embodiment or any combination of aspects of the leaf module according to the invention as described in the previous parts of this specification may be employed. When being employed within the multi-leaf collimator according to the invention, it is understood that the leaf module according to the invention and/or further aspects of the leaf module according to the optional embodiments as explained above, also aspects being combined, will yield the advantageous effects as described above also with relation to the multi-leaf collimator.

In a first further optional embodiment of the multi-leaf collimator according to the invention, respective leaf drive units being assigned to adjacent leaf units are arranged in an offset pattern. In such a way, adjacent leaf drive units will not interfere with each other, allowing to minimize the thickness of the leaves and increasing the number of leaf drive units. Preferably and optionally, in an embodiment, guiding rods interacting with the leaf drive units are attached to the leaves, wherein the attaching position of the guiding rods related to the leaves may also follow an offset pattern when regarding adjacent leaves.

In yet a further embodiment of the multi-leaf collimator according to the invention, two assemblies of leaf modules are provided, wherein each assembly comprises a plurality of leaf modules according to the invention, and wherein the leaf modules of each assembly face each other. Consequently, by adjusting the leaf units facing each other in their respective adjusting direction, an area of arbitrary shape, in particular any contour of a treatment object, for example a tumor, can be recreated for beam application.

Summarizing, the following embodiments are preferred embodiments of the present invention:

EMBODIMENT 1

A leaf module for a multi-leaf collimator, comprising a leaf unit and a leaf drive unit, wherein the leaf unit comprises a leaf for shielding beams from a selected area, wherein the leaf unit is mounted displaceably in an adjusting direction with relation to the leaf drive unit, wherein the leaf drive unit is designed to displace the leaf unit linearly in the adjusting direction, and wherein the leaf drive unit comprises at least one drive mechanism which operates based on piezoelectric actuation,
wherein the leaf drive unit thoroughly encloses the leaf unit within a plane being oriented substantially perpendicularly related to the adjusting direction.

EMBODIMENT 2

The leaf module according to the preceding embodiment, characterized in that the leaf drive unit is designed to displace the leaf unit in the adjusting direction and additionally provides guidance to the leaf unit with respect to any direction being oriented perpendicularly related to the adjusting direction.

EMBODIMENT 3

The leaf module according to the preceding embodiment, characterized in that the guidance of the leaf unit provided by the leaf drive unit is substantially free of slackness.

EMBODIMENT 4

The leaf module according to any one of the preceding embodiments, characterized in that the leaf drive unit exerts a friction force and/or a clamping force on the leaf unit when no displacement of the leaf unit takes place.

EMBODIMENT 5

The leaf module according to any one of the preceding embodiments, characterized in that one drive mechanism within the leaf drive unit encloses the leaf unit, or in that a plurality of separate drive mechanisms are arranged within the leaf drive unit in such manner that an enclosure of the leaf unit by the drive mechanisms is provided.

EMBODIMENT 6

The leaf module according to any one of the preceding embodiments, characterized in that at least one drive mechanism comprises a non-resonant piezoelectric motor.

EMBODIMENT 7

The leaf module according to any one of the preceding embodiments, characterized in that at least one drive mechanism comprises a piezoelectric motor generating motion of the leaf unit through succession of coordinated clamping/unclamping and expanding/contracting cycles.

EMBODIMENT 8

The leaf module according to any one of the preceding embodiments, characterized in that the leaf unit further comprises a guiding rod, wherein the guiding rod is a separate part being attached to the leaf, or wherein the guiding rod is an integral part of the leaf.

EMBODIMENT 9

The leaf module according to the preceding embodiment, characterized in that the guiding rod provides the portion of the leaf unit which is enclosed by the leaf drive unit.

EMBODIMENT 10

The leaf module according to any one of embodiments 8 or 9, characterized in that the guiding rod comprises ceramic material and/or in that the guiding rod is coated with ceramic material.

EMBODIMENT 11

The leaf module according to any one of embodiments 8 to 10, characterized in that the guiding rod is attached to the leaf by form-fitting and/or force-locking, in particular wherein the guiding rod is inserted into a channel located on the surface of the leaf, wherein the channel represents a negative pattern of the shape of the guiding rod.

EMBODIMENT 12

The leaf module according to any one of the preceding embodiments, characterized in that the leaf material comprises a high density material, in particular tungsten.

EMBODIMENT 13

A multi-leaf collimator, characterized by a plurality of leaf modules according to any one of the preceding embodiment.

EMBODIMENT 14

The multi-leaf collimator according to the preceding embodiment, characterized in that respective leaf drive units being assigned to adjacent leaf units are arranged in an offset pattern.

EMBODIMENT 15

The multi-leaf collimator according to any one of embodiments 13 or 14, characterized by two assemblies of leaf modules, wherein each assembly comprises a plurality of leaf modules according to any one of embodiments 1 to 12, and wherein the leaf modules of each assembly face each other.

In the following, the invention will further be explained by way of both schematic and exemplary drawings. In the figures, identical reference numbers refer to identical components or components having the same or similar functions. Thus, such components and referring reference numbers might not be explained with regard to each figure, and explanations given on the occasion of preceding figures are referred to in such cases. In the figures, aspects of the leaf module and also is aspects of the multi-leaf collimator according to the invention will be explained referring to preferred embodiments. While explaining aspects of the leaf module according to the invention, reference will also be made to aspects of the multi-leaf collimator according to the invention. The exemplary embodiments related to in the figures and the referring explanations are merely given for illustrative purposes, and the invention is not restricted to these embodiments.

Shown are in

Figure 2:
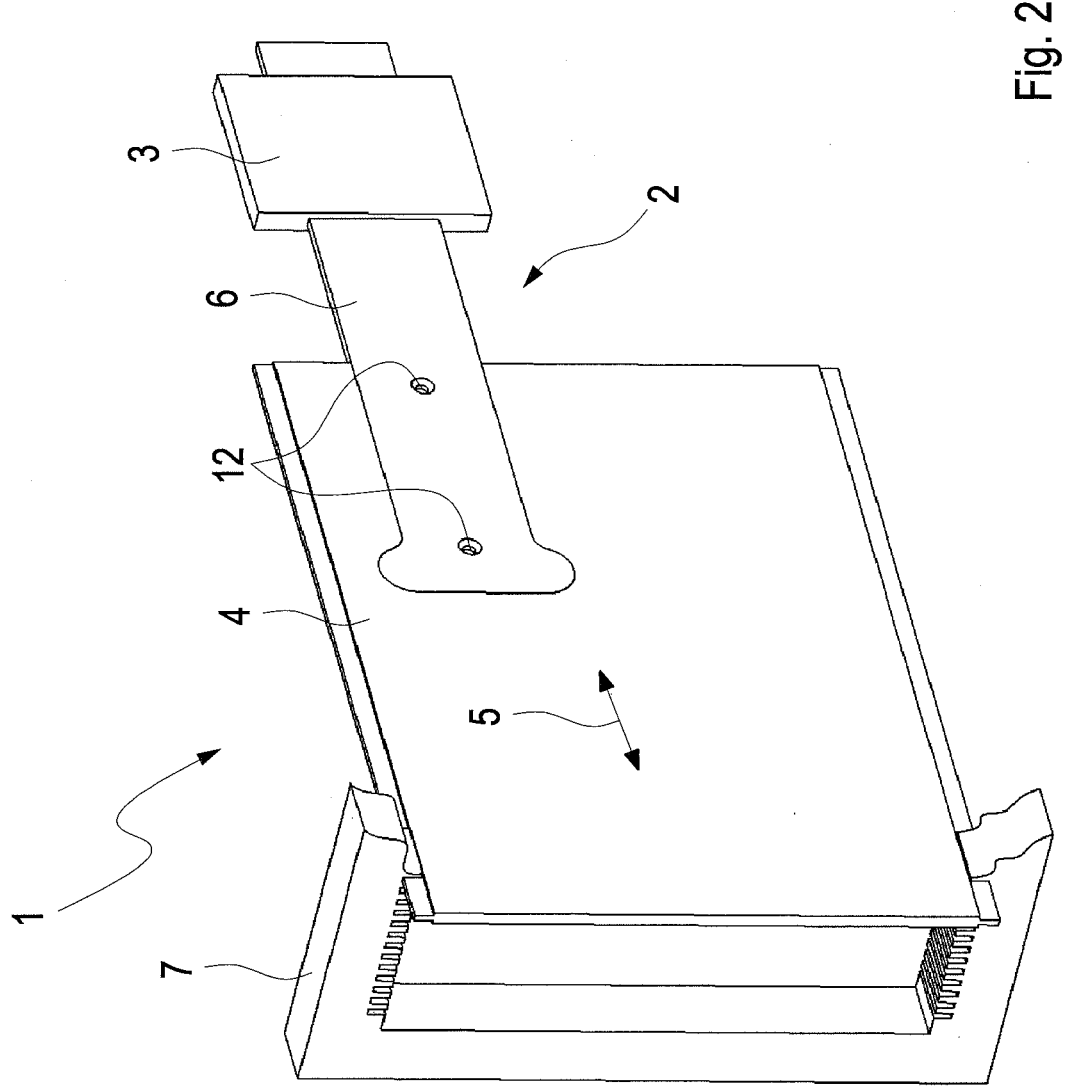
Figure 3:
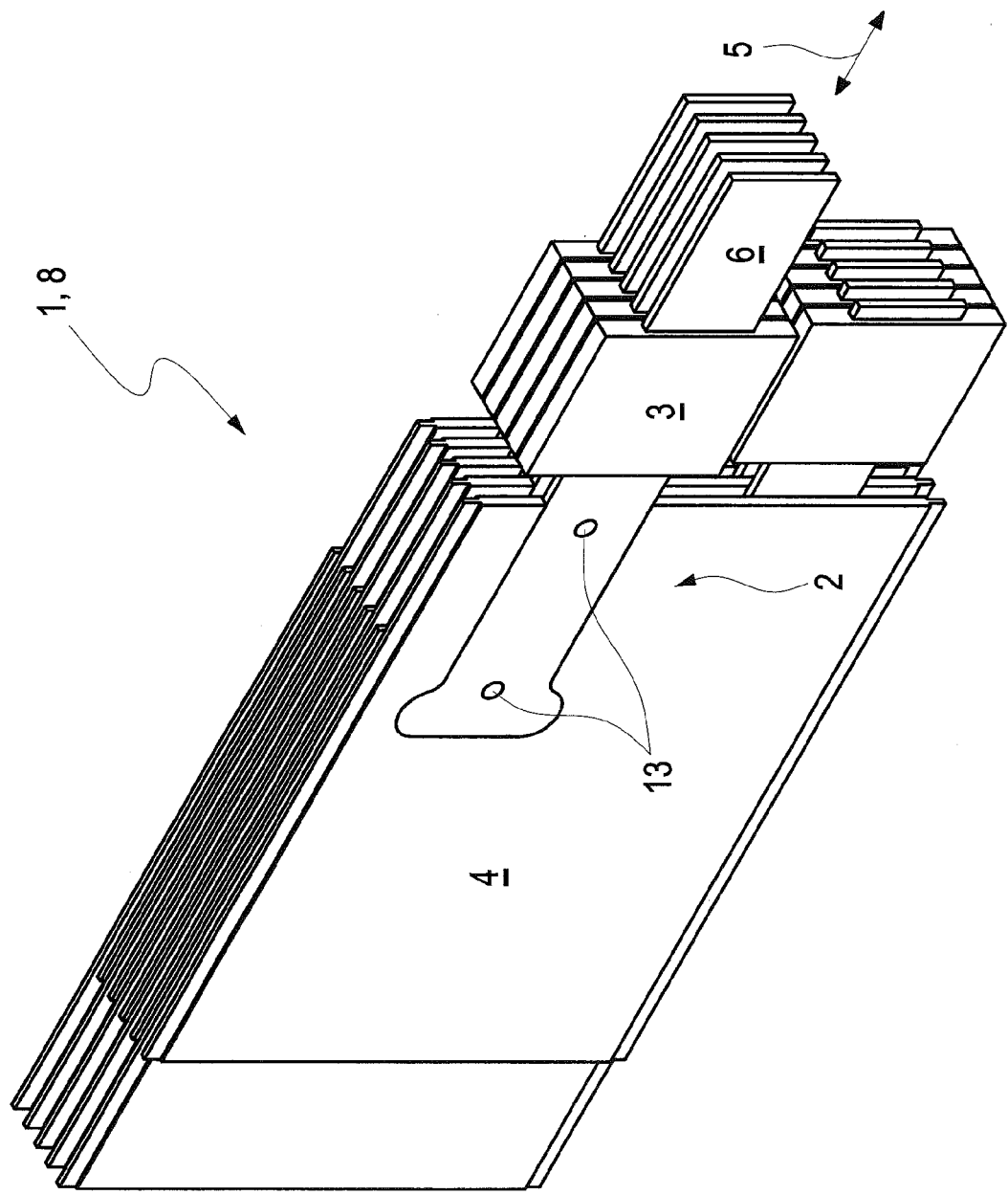
Figure 4:
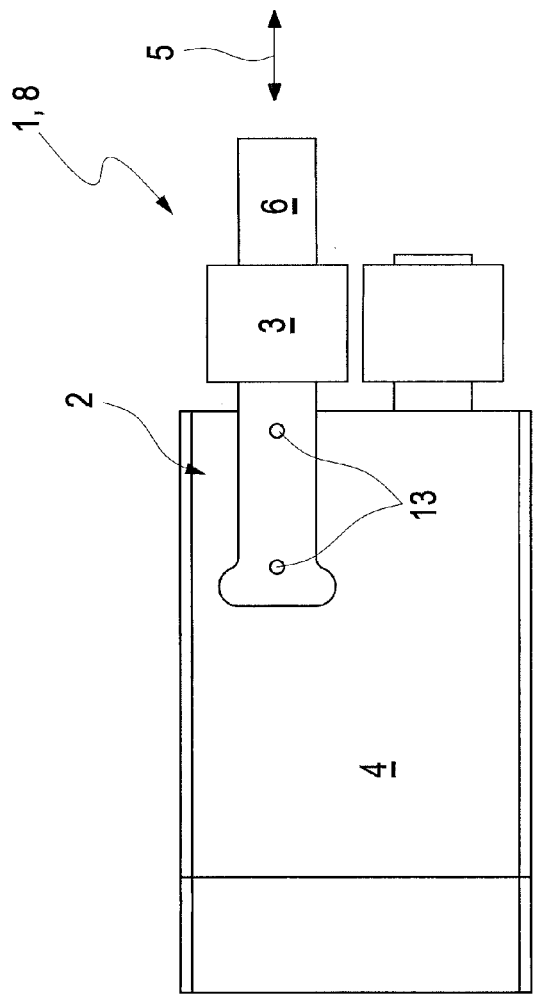
Figure 5:
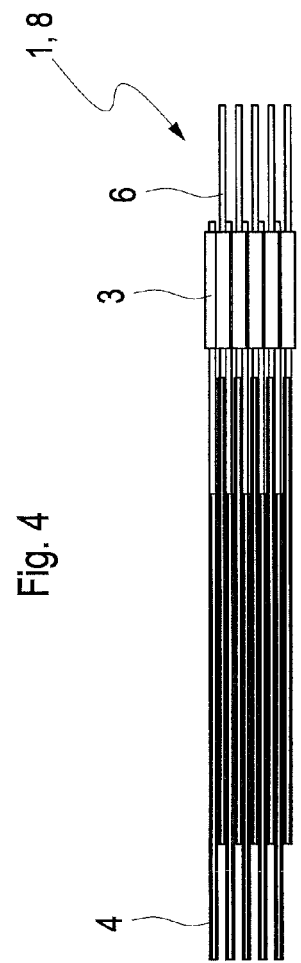
Figure 6:
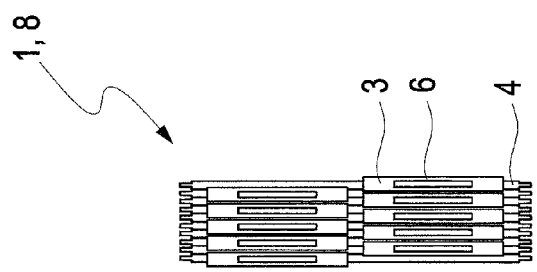
Figure 7:
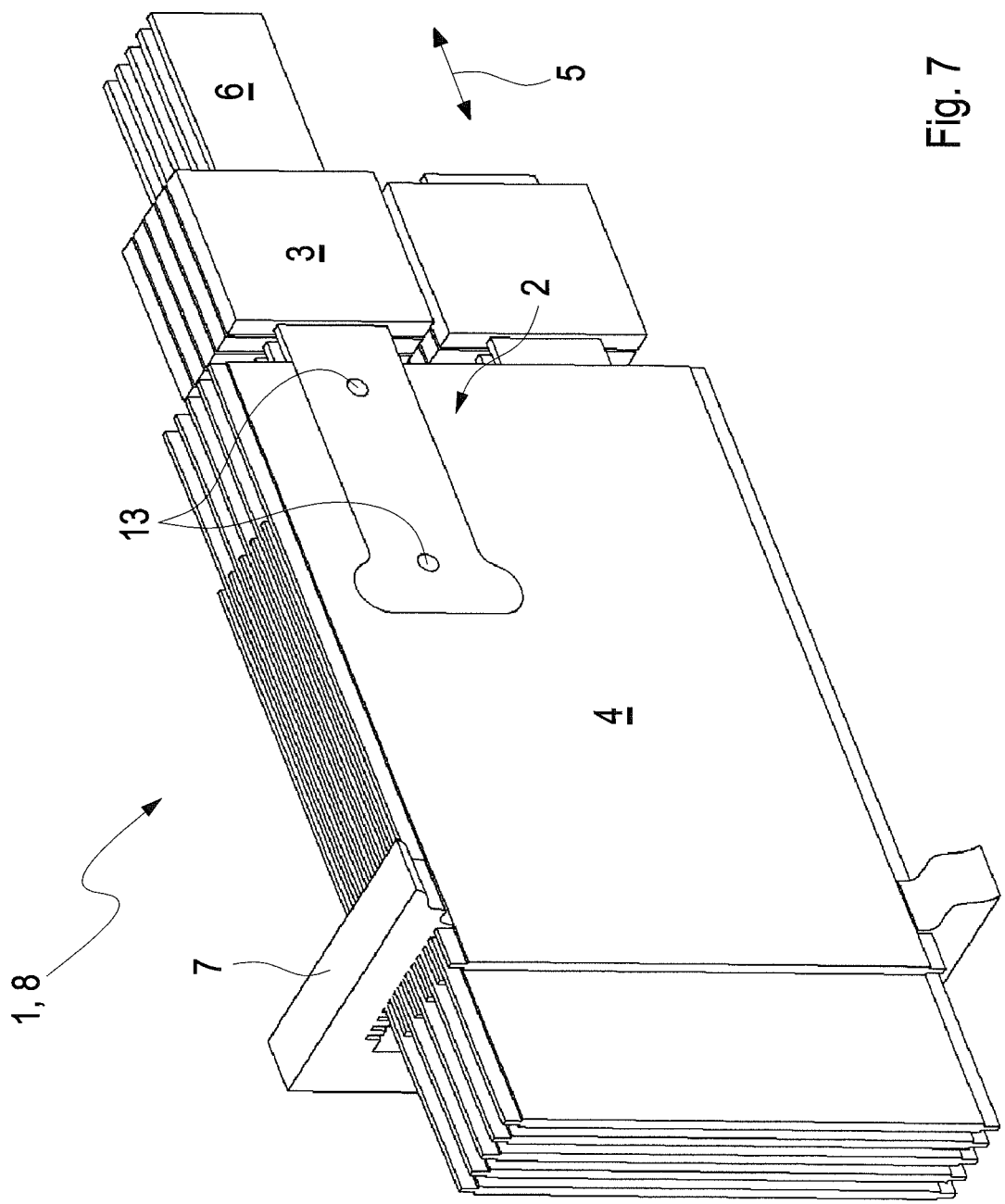
Figure 8:
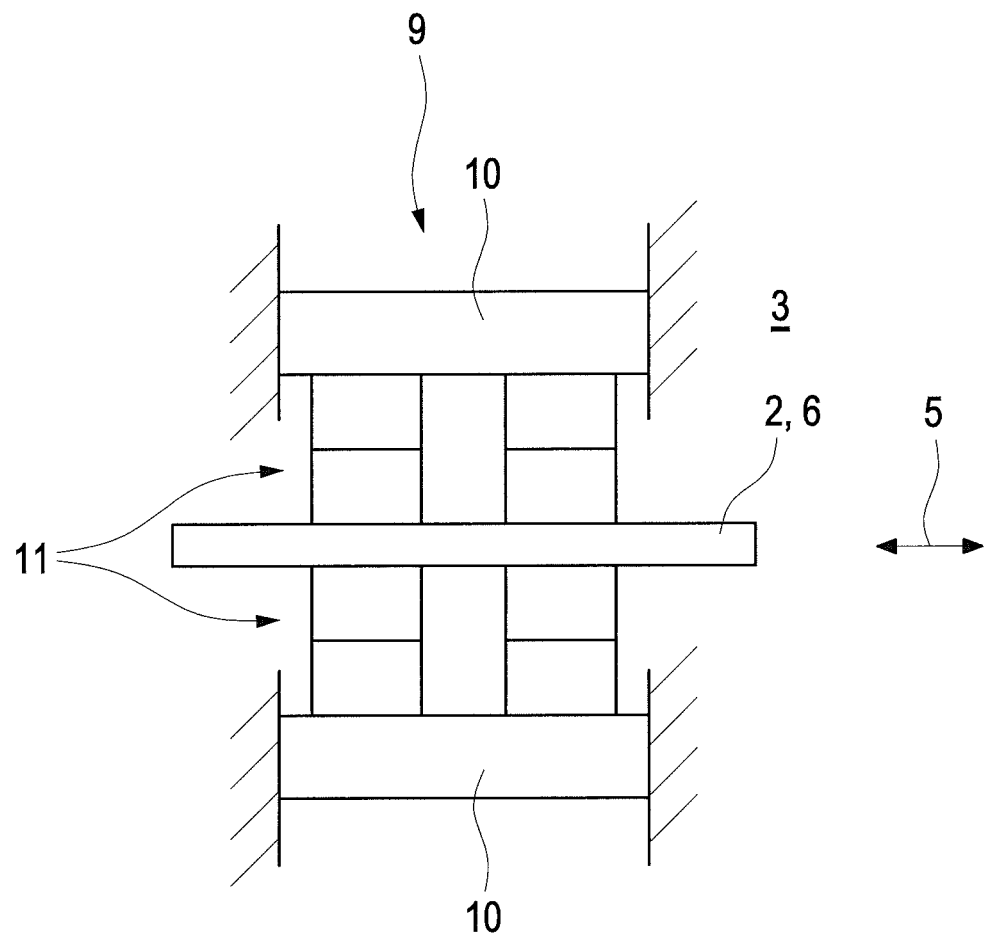
Figure 9:
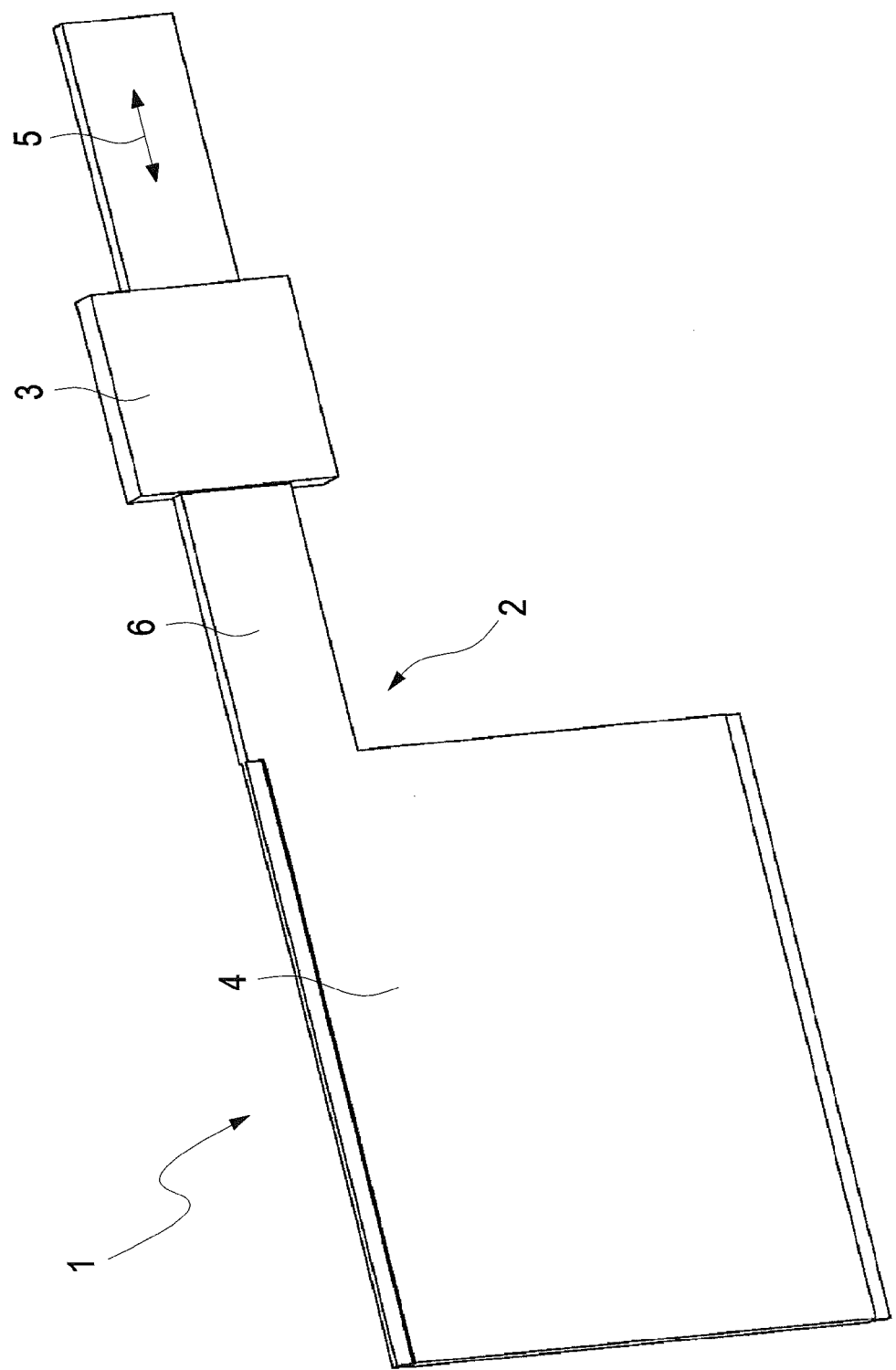
Figure 10:
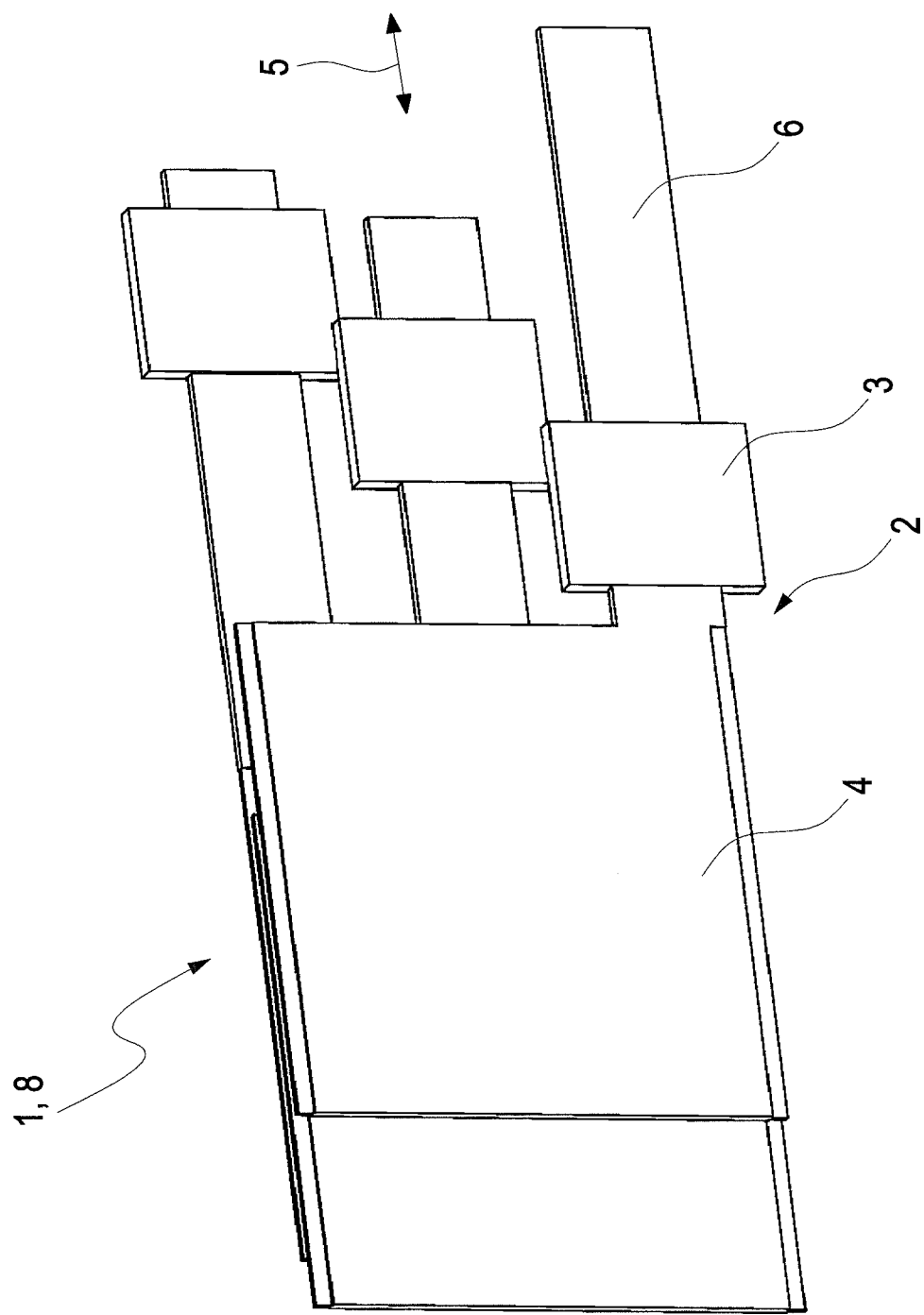
Figure 11:
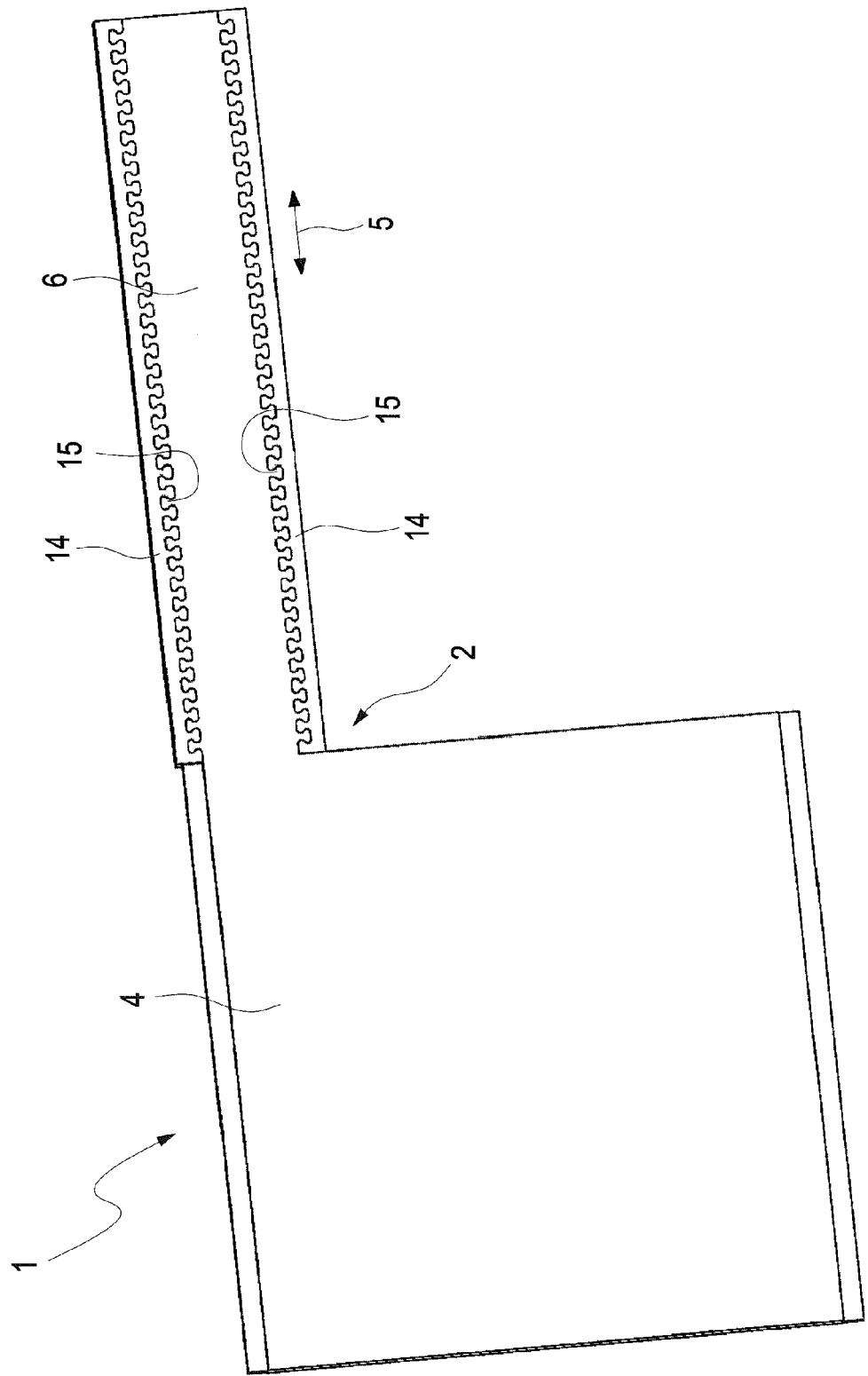

FIG. 1 in both a side and a perspective view a leaf module according to the invention, FIG. 2 a leaf module according to the embodiment shown in FIG. 1 being arranged in an optional linear guiding unit, FIG. 3 a perspective view of an assembly of leaf modules according to the invention, wherein the assembly may be employed in a multi-leaf collimator according to the invention, FIG. 4 a side view of the assembly according to FIG. 3, FIG. 5 a top view of the assembly according to FIGS. 3 and 4, FIG. 6 a rear view of the assembly according to FIGS. 3-5, FIG. 7 a perspective view of the assembly of leaf modules according to FIGS. 3-6 being arranged in an optional linear guiding unit, FIG. 8 a schematic sketch of a piezoelectric drive mechanism preferably used in a leaf module according to the invention, FIG. 9 in a perspective view another leaf module according to the invention, wherein a guiding rod is an integral part of the leaf, FIG. 10 a perspective view of an assembly of leaf modules, wherein, in each leaf module, a guiding rod is an integral part of the leaf, and FIG. 11 a sectional view of a further leaf unit for a further embodiment of a leaf module according to the invention, wherein an integral guiding rod comprises ceramic rails.

FIG. 1 discloses, both in a side and a perspective view, a leaf module 1 according to the invention. The leaf module 1 generally comprises a leaf unit 2 and a leaf drive unit 3. The leaf unit 2 comprises a leaf 4 for shielding beams from a selected area, in particular when being arranged in a multi-leaf collimator. In order to allow the shielding of beams, the leaf 4 comprises tungsten material.

Further, in order to allow selecting an area from which beams are shielded, the leaf unit 2 is mounted displaceably in an adjusting direction 5 with relation to the leaf drive unit 3. The leaf drive unit 3 is designed to displace the leaf unit 2 comprising the leaf 4 linearly in the adjusting direction 5. For this purpose, the leaf drive unit 3 comprises at least one piezoelectric drive mechanism being arranged inside of the leaf drive unit 3 and thus not shown in this drawing. The drive mechanism operates based on piezoelectric actuation to allow high precision of adjustability of leaf unit 2/leaf 4 and compact shaping of the leaf module 1.

In order to further enhance compactness of the leaf module 1 design and also improve precision and stability of the adjustability of leaf unit 2, the leaf drive unit 3 thoroughly encloses the leaf unit 2 within a plane being oriented substantially perpendicularly related to the adjusting direction 5.

In order to enclose the leaf unit 2 in the manner described, the leaf drive unit 3 features a block-like shape with a central aperture extending longitudinally in the adjusting direction 5. This aperture within the leaf drive unit 3 is shaped to snugly enclose the leaf unit 2 in order to allow the leaf drive unit 3 to both displace the leaf unit 2 in the adjusting direction 5 and additionally provide guidance to the leaf unit 2 to avoid unwanted deviations of the leaf 4 from the adjusting direction 5. With other words, the aperture extending through the leaf drive unit 3 fits the outer shape of the leaf unit 2 in such a way that the guidance of the leaf unit 2 provided by the leaf drive unit 3 is substantially free of slackness. By this fitting technique, it is possible that the leaf drive unit 3 exerts a friction force and/or a clamping force on the leaf unit 2 when a displacement and/or when no displacement of the leaf unit 2 takes place.

One further important feature characterizing the embodiment of the leaf module 1 as shown in the drawings of FIG. 1 is obtainable from said Figure. Here, the leaf unit 2 not only comprises a leaf 4, but further comprises a guiding rod 6, wherein the guiding rod 6 is attached to the leaf 4. Here, the guiding rod 6 is attached to the leaf 4 by rivets 12. Also, according to the embodiment disclosed, not the leaf 4, but the guiding rod 6 provides the portion of the leaf unit 2 which is enclosed by the leaf drive unit 3. With this aspect, improved adjusting and guiding of the leaf unit 2 in the adjusting direction 5 is provided. Due to the compactness of the contacting portion of leaf drive unit 3 and guiding rod 6, a large number of leaf modules 1 may be arranged in an irradiation head of confined size. Also, a larger number of leaves 4 with less thickness may be arranged adjoiningly.

For improved interaction between the leaf drive unit 3 and the guiding rod 6 with enhanced exerting of friction and/or clamping forces between the leaf drive unit 3 and the guiding rod 6, the latter comprises ceramic material.

Also, in order to allow the stacking of large numbers of leaves 4 adjacently and for effective shielding of beams, the guiding rod 6 is attached to the leaf 4 in such manner that the guiding rod 6 is inserted into a channel located on the surface of the leaf 4, wherein the channel represents a negative pattern of the shape of the guiding rod 6. In this way, both form-fitting and/or force-locking of the guiding rod 6 to the leaf 4 may result.

FIG. 2 discloses a perspective view of a leaf module 1 according to the invention and according to the embodiment shown in FIG. 1 which is arranged in an optional linear guiding unit 7. The linear guiding unit 7 features a U-like shape, with a multitude of slots being machined in opposite brackets. Within the linear guiding unit 7, a multitude of leaf modules 1 may be arranged adjacently to faint an assembly of leaf modules 1. In order to fit the slots within the linear guiding unit 7, upper and lower end portions of the leaf 4 comprise a corresponding shape. It should be noted that due to the enclosing of leaf unit 2 by the leaf drive unit 3, a very high quality in adjusting and/or guiding the leaf unit 2 within the adjusting direction 5 is providable. Thus, in most cases, an additional linear guiding unit 7 may be designed interacting with the leaf 4 with larger values of tolerance and thus less friction, or an additional linear guiding unit 7 may even be completely renounced. However, employing an optional linear guiding unit 7 may be envisaged when using very large leaves 4.

FIG. 3 discloses a perspective view of an assembly 8 of leaf modules 1 for being used in a multi-leaf collimator in accordance with the present invention. For building the assembly 8, a plurality of leaf modules 1 according to the invention and according to the embodiment shown in FIG. 1 and FIG. 2 are arranged adjacently, or, with other words, stacked sideways. It should be noted that here, the guiding rod 6 is attached to the leaf 4 by pins 13 instead of rivets. Within the assembly 8, respective guiding rods 6 and leaf drive units 3 being assigned to adjacent leaf units 2 are arranged in an offset pattern. This means that in one leaf unit 2 the guiding rod 6 and the leaf drive unit 3 are attached to the upper part of the leaf 4, whereas in the adjacent, neighboring leaf unit 2, the guiding rod 6 and the leaf drive unit 3 are attached to the lower part of the leaf 4. In this way, guiding rods 6 and leaf drive units 3 of adjacent leaf modules 1 will not interfere with each other, thus allowing the construction of very compact assemblies 8 comprising very thin leaves 4.

FIG. 4 discloses a side view of the assembly 8 according to FIG. 3. It is well obtainable from this drawing that the guiding rods 6 and the leaf drive units 3 of adjacent leaf modules 1 exhibit a distinct clearance in the vertical direction, thus not interfering with each other.

FIG. 5 shows a top view of assembly 8. This drawing is very explicit in showing that within assembly 8, adjacent leaves 4 are being stacked in such a way that a full shielding of beams from a selected area can be implemented, even though the leaf drive units 3 may feature a larger thickness than the leaves 4.

FIG. 6 shows a rear view of assembly 8. This drawing again shows that basically no clearance exists between adjacent leaves 4. However, guidance rods 6 and leaf drive units 3 of neighboring leaf modules 1 do possess sufficient clearance with relation to each other and will not interfere when adjusting the leaf units 2.

FIG. 7 discloses an assembly 8 of leaf modules 1 according to the embodiment of the assembly shown in FIGS. 3-6. However, the assembly 8 according to this figure is additionally arranged in a linear guiding unit 7 as already described with relation to FIG. 2. Concerning the optional and additional linear guiding unit 7, reference to the explanations made concerning FIG. 2 is made.

FIG. 8 shows a schematic sketch of a preferred embodiment of two oppositely arranged drive mechanisms 9 being arranged inside the leaf drive unit 3. With other words, the leaf drive unit 3, according to this embodiment, will serve as a housing for the drive mechanisms 9.

Also, embodiments may be implemented in which one drive mechanism 9 within the leaf drive unit 3 encloses the leaf unit 2, or wherein a plurality (more than two) of separate drive mechanisms 9 are arranged within the leaf drive unit 3. In this way, an enclosure of the leaf unit 2 by one, two or a plurality of drive mechanisms 9 may be provided. However, if the drive mechanisms 9 will not themselves enclose the leaf unit 2, it is still essential according to the invention that at least the leaf drive unit 3 thoroughly encloses the leaf unit 2.

The two opposing drive mechanisms 9 according to the sketch in FIG. 8 each comprise a base plate 10 and two piezo actuators 11 extending from the base plate 10 to the leaf 4. The piezo actuators 11 each comprise a piezo stack. In this way, a drive mechanism 9 comprising a non-resonant piezoelectric motor may be provided. The drive mechanism 9 being a non-resonant piezoelectric motor generates motion of the leaf unit 2 through succession of coordinated clamping/unclamping and expanding/contracting cycles of the piezo actuators 11. During displacement and also when not displacing the leaf unit 2, the drive mechanisms 9 exert a friction force and a clamping force on the leaf unit 2, thus providing precise adjustability and precise linear guidance to the leaf unit 2. In particular, for this purpose, the base plates 10 may be subject to a preload force being oriented towards the leaf unit 2.

FIG. 9 shows a perspective view of a further embodiment of leaf module 1 according to the invention. For the explanation of the different parts of leaf module 1, reference to the description of FIG. 1 is made. However, here, guiding rod 6 is formed as an integral part of the leaf 4. With this embodiment, the manufacturing of the leaf unit 2 may be facilitated, and/or the deviating of the plane of leaf 4 from the plane in which guiding rod 6 extends may be minimized or even completely avoided.

FIG. 10 discloses a perspective view of an assembly 8 of leaf modules 1 according to the invention, wherein—comparable to FIG. 9—the guiding rod 6 forms an integral part of the leaf 4 within each leaf unit 2 and each leaf module 1. It is well visible that in adjacent leaf modules 1, the guiding rods 6 are formed at differing locations relating to leaf 4, so that leaf drive units 3 of adjacent leaf modules 1 will not interfere with each other when leaf modules 1 are being stacked to form an assembly 8. In this regard, reference is made to the explanation of FIGS. 3-6.

Finally, FIG. 11 shows a sectional side view of a further leaf unit 2 of a leaf module according to the invention. The leaf unit 2 shown in FIG. 11 may be compared to the leaf unit of FIG. 9, as the guiding rod 6 forms an integral part of the leaf 4. However, additionally, the guiding rod 6 of leaf unit 2 according to FIG. 11 further comprises two ceramic rails 14 on both its upper and lower side. The ceramic rails 14 provide an advantageous interaction with the drive mechanism (not shown here) of the leaf module, wherein beneficial clamping and/or frictional forces may be transmitted to the guiding rod 6 via the ceramic rails 14. Both ceramic rails 14 are fixed to the guiding rod 6 by a toothing 15.

LIST OF REFERENCE SYMBOLS

1 leaf module
2 leaf unit
3 leaf drive unit
4 leaf
5 adjusting direction
6 guiding rod
7 linear guiding unit
8 assembly (of leaf modules)
9 drive mechanism
10 base plate (drive mechanism)
11 piezo actuator
12 rivet
13 pin
14 ceramic rail
15 toothing

The invention claimed is:

1. A leaf module for a multi-leaf collimator, comprising a leaf unit and a leaf drive unit, wherein
   the leaf unit comprises a leaf for shielding beams from a selected area,
   the leaf unit is mounted displaceably in an adjusting direction with relation to the leaf drive unit, wherein
   the leaf drive unit is designed to displace the leaf unit linearly in the adjusting direction, and
   the leaf drive unit comprises at least one drive mechanism which operates based on piezoelectric actuation, wherein the leaf drive unit thoroughly encloses a portion of the leaf unit, wherein the leaf drive unit encloses the leaf unit in a plane that extends substantially perpendicular to the adjusting direction.

2. The leaf module according to claim 1, characterized in that the leaf drive unit is designed to displace the leaf unit in the adjusting direction and additionally provides guidance to the leaf unit with respect to any direction being oriented perpendicularly related to the adjusting direction.

3. The leaf module according to claim 2, characterized in that the guidance of the leaf unit provided by the leaf drive unit is substantially free of slackness.

4. The leaf module according to claim 1, characterized in that the leaf drive unit exerts one or more of a friction force and a clamping force on the leaf unit when no displacement of the leaf unit takes place.

5. The leaf module according to claim 1, characterized in that one drive mechanism within the leaf drive unit encloses the leaf unit, or in that a plurality of separate drive mechanisms are arranged within the leaf drive unit in such manner that an enclosure of the leaf unit by the drive mechanisms is provided.

6. The leaf module according to claim 1, characterized in that at least one drive mechanism comprises a non-resonant piezoelectric motor.

7. The leaf module according to claim 1, characterized in that at least one drive mechanism comprises a piezoelectric motor generating motion of the leaf unit through succession of coordinated clamping/unclamping and expanding/contracting cycles.

8. The leaf module according to claim 1, characterized in that the leaf unit further comprises a guiding rod, wherein the guiding rod is a separate part being attached to the leaf, or wherein the guiding rod is an integral part of the leaf.

9. The leaf module according to claim 8, characterized in that the guiding rod provides the portion of the leaf unit which is enclosed by the leaf drive unit.

10. The leaf module according to claim 8, characterized in that the guiding rod comprises ceramic material.

11. The leaf module according to claim 8, characterized in that the guiding rod is attached to the leaf by one or more of form-fitting and force-locking.

12. The leaf module according to claim 1, characterized in that the leaf material comprises a high density material.

13. A multi-leaf collimator, comprising a plurality of leaf modules according to claim 1.

14. The multi-leaf collimator according to claim 13, characterized in that respective leaf drive units being assigned to adjacent leaf units are arranged in an offset pattern.

15. The multi-leaf collimator according to claim 13, characterized by two assemblies of leaf modules, wherein each assembly comprises the plurality of leaf modules, and wherein the leaf modules of each assembly face each other.

16. The leaf module according to claim 11, wherein the guiding rod is inserted into a channel located on the surface of the leaf, wherein the channel represents a negative pattern of the shape of the guiding rod.

17. The leaf module according to claim 12, wherein the high density material is tungsten.

18. The leaf module according to claim 8, characterized in that the guiding rod is coated with ceramic material.

\* \* \* \* \*